United States Patent [19]

Gätzi et al.

[11] 4,285,959
[45] Aug. 25, 1981

[54] 3-(N-1,3,4-THIADIAZOLYL-2)-AMINOAL-KYL-ALKYL-ACRYLATES AND USE THEREOF AS BACTERICIDES

[75] Inventors: Karl Gätzi, Basel; Hanspeter Baumann, Reinach, both of Switzerland; Walter Kunz, Manchester, England; Bernhard Gloor, Pratteln, Switzerland

[73] Assignee: Ciba-Geigy Corporation, Ardsley, N.Y.

[21] Appl. No.: 147,457

[22] Filed: May 7, 1980

[30] Foreign Application Priority Data

May 18, 1979 [CH] Switzerland ............... 4670/79
Apr. 14, 1980 [CH] Switzerland ............... 2857/80

[51] Int. Cl.$^3$ ............... A01N 43/82; C07D 285/08; C07D 417/12
[52] U.S. Cl. ............... 424/270; 424/263; 546/277; 548/138; 548/139
[58] Field of Search ............... 548/138, 139; 424/263, 424/270; 546/277

[56] References Cited

U.S. PATENT DOCUMENTS 3,794,665  2/1974  Berkelhammer et al. ............... 548/139

OTHER PUBLICATIONS

Szmuszkovicz et al., "Advances in Organic Chemistry, Methods and Results", (Interscience, New York, 1963), pp. 9–12, 47–55.

*Primary Examiner*—Alton D. Rollins
*Attorney, Agent, or Firm*—Frederick H. Rabin

[57] ABSTRACT

Novel 2-amino-thiadiazole derivatives of the formula

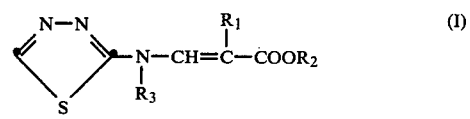

are described. In the formula, $R_1$ is hydrogen or $C_1$–$C_4$ alkyl; $R_2$ is $C_1$–$C_4$ alkyl; $R_3$ is hydrogen or the group —CO—$R_4$, in which $R_4$ is alkoxyalkyl, $C_3$–$C_6$ cycloalkyl, or is $C_2$–$C_4$ alkenyl each of which is unsubstituted or mono- or polysubstituted by halogen, or is furyl, thienyl, pyridyl or phenyl, each of which is unsubstituted or mono- to tetrasubstituted by $C_1$–$C_4$ alkyl, halogen, cyano, nitro, alkoxy, alkylthio, alkylsulfonyl or amino. These compounds possess useful bactericidal properties and can be used in particular for controlling phytopathogenic bacteria without damaging the treated cultivated plants. In comparison to aminothiadiazoles of the prior art, the compounds of this invention cause no tetratogenic side-effects.

12 Claims, No Drawings

3-(N-1,3,4-THIADIAZOLYL-2)-AMINOALKYL-ALKYL-ACRYLATES AND USE THEREOF AS BACTERICIDES

The present invention relates to compounds of the formula I

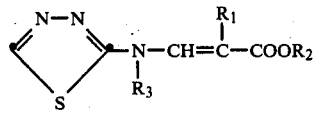

wherein $R_1$ is hydrogen or $C_1$–$C_4$alkyl, $R_1$ is $C_1$–$C_4$alkyl, $R_3$ is hydrogen or the group —CO—$R_4$, in which $R_4$ is alkoxyalkyl, $C_3$–$C_6$cycloalkyl, or is $C_1$–$C_4$alkyl or $C_2$–$C_4$alkenyl each of which is unsubstituted or mono- or polysubstituted by halogen, or is furyl, thienyl, pyridyl or phenyl, each of which is unsubstituted or mono- to tetrasubstituted by $C_1$–$C_4$alkyl, halogen, cyano, nitro, alkoxy, alkylthio, alkylsulfonyl or amino.

Depending on the indicated number of carbon atoms, alkyl by itself or as moiety of another substituent denotes e.g. methyl, ethyl, propyl, butyl, pentyl, hexyl, heptyl, octyl etc., as well as their isomers, e.g. isopropyl, isobutyl, tert-butyl, isopentyl etc. Alkenyl is e.g. propenyl-(1), allyl, butenyl-(1), butenyl-(2) or butenyl-(3). Cycloalkyl is e.g. cyclopropyl, cyclobutyl, cyclopentyl or cyclohexyl. Halogen is e.g. fluorine, chlorine, bromine or iodine.

Compounds of the formula I are stable substances. They have a very advantageous microbicidal activity spectrum and act in particular against phytopathogenic microorganisms, especially bacteria which are injurious to plants.

An interesting group of bactericides comprises compounds of the formula I, wherein $R_3$ is hydrogen.

The following individual compounds of the formula I are especially preferred on account of their very good bactericidal action:

3-(N-1,3,4-thiadiazolyl-2)-amino-2-methyl-methyl acrylate, 3-(N-1,3,4-thiadiazolyl-2)-amino-2-methyl-ethyl acrylate, 3-(N-1,3,4-thiadiazolyl-2)-amino-2-methyl-n-propyl acrylate, 3-(N-1,3,4-thiadiazolyl-2)-amino-2-ethyl-ethyl acrylate, 3-(N-1,3,4-thiadiazolyl-2)-amino-2-isopropyl-methyl acrylate.

The compounds of the formula I can be obtained by the procedures which are described in detail hereinafter. Intermediates formed during the reaction can be isolated before further processing, but it is also possible to carry out the reaction without isolation of the intermediates. In formulae II, III, IV and also $R_4COOH$, the substituents $R_1$, $R_2$, $R_3$ and $R_4$ are as defined for formula I. X represents one of the customary leaving groups, e.g. alkoxy, benzenesulfonyloxy, p-bromobenzenesulfonyloxy, p-tosyloxy, lower alkylsulfonyloxy such as mesyloxy, or is especially halogen such as fluorine, chlorine, bromine, iodine, with chlorine or bromine being preferred.

The compounds of the formula I are obtained either by (a) condensing 2-amino-1,3,4-thiadiazole of the formula II

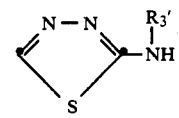

wherein $R_3'$ is hydrogen, with a compound of the formula III

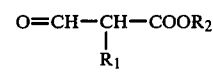

with elimination of water, and subsequently, if desired, N-acylating the condensate with an acid $R_4COOH$ or preferably with a reactive acid derivative, or (b) reacting a compound of the formula II, wherein $R_3'$ has the same meaning as $R_3$, with a compound of the formula IV

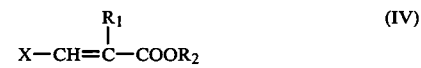

preferably in the presence of a base and with the elimination of a compound of the formula H-X, and, if desired, N-acylating the reaction product as described in (a) if $R_3'$ is hydrogen.

All reaction steps are advantageously carried out in the presence of an organic solvent or diluent which is inert to the reactants. As diluent it is often possible to use an excess of a reactant, for example excess acylating agent in the N-acylation.

Examples of suitable reaction media for the above reactions of the compounds of the formulae II and III are aliphatic and aromatic hydrocarbons such as benzene, toluene, xylenes, petroleum ether; halogenated hydrocarbons such as chlorobenzenes, carbon tetrachloride, tetrachloroethylene; esters such as ethyl acetate, propyl acetate, butyl acetate; ethers and ethereal compounds such as dialkyl ethers (diisopropyl ether, tert-butylmethyl ether etc.), anisole, dioxane, dimethoxyethane; alcohols such as ethanol, propanol, butanol and methyl cellosolve; nitriles such as acetonitrile, propionitrile etc., or mixtures of such solvents.

In the condensation reaction, the presence of an acid, basic or neutral condensation agent or acid acceptor can be advantageous. Examples of suitable condensation agents are strong acids such as sulfonic acids (p-toluenesulfonic acid, benzenesulfonic acid), phosphoric acid; amines such as pyridine, 4-dimethylaminopyridine, 4-pyrrolidylpyridine, piperidine, triethylamine, triethylenediamine, N,N-dimethylaniline; anhydrides such as acetic anhydride, as well as molecular sieves, and also compounds such as dicyclohexylcarbodiimide.

The reaction temperature in the condensation reaction to produce the enamine is normally in the range between 0° and 180° C., with the preferred range being between 50° and 150° C., or the boiling point of the solvent or solvent mixture.

The reactions with acrylic acid derivatives of the formula IV are advantageously performed in an aprotic solvent in the presence of a strong base. Suitable bases are oxides, hydroxides, hydrides, carbonates and hydrocarbonates of alkali metals and alkaline earth metals, alkali metal acetates and organometal compounds such as butyl lithium.

To hasten the reaction rate, it can be advantageous to conduct this reaction in the presence of a phase transfer catalyst. Examples of such catalysts are: tetraalkylammonium halides, tetraalkyl hydrogen sulfates and tetraalkyl hydroxides, e.g. tetrabutyl ammonium chloride, tetrabutyl ammonium bromide and tetrabutyl ammonium iodide; triethylbenzyl ammonium chloride and bromide; tetrapropyl ammonium chloride, bromide and iodide. Suitable phase transfer catalysts are also phosphonium salts.

The N-acylation reactions are performed either by reaction with the acid $R_4COOH$ itself, or advantageously with a reactive acid derivative such as an ester, acid anhydride or acid halide, preferably an acid chloride or acid bromide. It can be of advantage to carry out the acylation in the presence of a reaction catalyst such as dimethyl formamide.

The reaction temperatures are in the range between 0° and 180° C., with the preferred range being between 0° and 150° C., or the boiling point of the solvent or solvent mixture. It is often advantageous to employ acid acceptors or condensation agents. Suitable examples are: amines such as trialkylamines (trimethylamine, triethylamine, tripropylamine etc.), pyridine and pyridine bases (4-dimethylaminopyridine, 4-pyrrolidylaminopyridine etc), oxides, hydroxides, carbonates and hydrogen carbonates of alkyl metals and alkaline earth metals as well as alkali metal acetates.

Hydrogen halide formed during the reaction can also often be expelled from the reaction mixture by the introduction of an inert gas, e.g. nitrogen, or bound with the aid of molecular sieves. All reaction steps are preferably carried out under normal pressure.

The starting materials of the formulae II, III and IV are generally known or they can be prepared by methods which are known per se.

All partial steps of the described process are to be considered as falling within the scope of the invention.

Related 2-amino-1,3,4-thiadiazole derivatives, among which is also the compound of the formula II, are known from U.S. Pat. No. 3,891,762. Their bactericidal action in plants is also described in this publication. It has been observed, however, that the compounds disclosed in the above patent specification possess a teratogenic action [cf. Teratology 7, 65 (1973); 9, 179 (1974) and 10, 90 (1964)]. Surprisingly, the compounds of the present invention do not have this serious side-effect (cf. the biological Examples). Furthermore, in contrast to the compounds of this invention, a number of the known compounds are phytotoxic.

Surprisingly, it has now been found that compounds of the formula I possess, for practical purposes, a very advantageous microbicidal activity spectrum. Their principal field of use resides in the control of harmful microorganisms, especially of phytopathogenic bacteria. Compounds of the formula I can be employed in particular for protecting cultivated plants without damaging these by undesirable side-effects, such as phytotoxicity. Examples of cultivated plants within the scope of this invention are: cereal crops, rice, citrus fruit, cotton, vegetables (e.g. tomatoes, paprika, cabbage, potatoes, carrots etcc), walnut trees, fruit trees (e.g. Prunus species, apple, pear and cherry trees), ornamentals (e.g. geraniums, begonia and many other species). This list constitutes only the most important and most endangered cultivated plants and will of course be construed as including related species or associated plants.

The compounds of the formula I can be used in particular against Xanthomonadae (e.g. *Xanthomonas ovyzae, Xanthomonas citri, Xanthomonas compestis, Xanthomonas malvacearum* etc), and also against phytopathogenic species of the genera Pseudomonas, Erwinia, Agrobacterium and Corynebacterium, namely in all areas in which such pathogens are found and develop, including host plants from the weed flora.

With the compounds of the formula I it is possible to inhibit or destroy the bacteria which infect plants or parts of plants (fruit, blossoms, leaves, stems, tubers, roots) in crops of useful plants, while parts of plants which grow later are protected against such infection. In addition, the compounds of the formula I have a systemic action.

The presence of a double bond in the molecule results in the formation of cis/trans-isomers which differ in their biological properties. Those compounds in which thiadiazolylamine group and carboxyl group are in the transposition to each other are strongly active bactericides.

The compounds of the formula I can be used by themselves or together with suitable carriers and/or other adjuvants. Suitable carriers and adjuvants can be solid or liquid and correspond to the substances normally used in the art of formulation, for example natural or regenerated mineral substances, solvents, dispersants, wetting agents, tackifiers, thickeners, binders or fertilisers.

For application the compounds of the formula I may be processed to the following formulations (in which the percentages refer to advantageous amounts of active ingredient):

Solid formulations:

dusts, tracking agents (up to 10%), granules (coated granules, impregnated granules and homogeneous granules); pellets (1 to 80%);

Liquid formulations:

(a) active ingredient concentrates which are dispersible in water: wettable powders, pastes (25–90% in commercial packs, 0.01 to 15% in ready-for-use solutions); concentrated emulsions and solutions (10 to 50%; 0.01 to 15% in ready-for-use solutions).

(b) Solutions, aerosols.

The content of active ingredient in the above described compositions is between 0.1 and 95% by weight. Such compositions likewise fall within the scope of this invention.

It will be understood that the compounds of the formula I can be used together with other suitable pesticides, e.g. fungicides, bactericides, insecticides, acaricides, herbicides or plant growth substances, in order to adapt them to prevailing circumstances and to broaden their activity spectrum.

Accordingly, the invention also relates to the use of the compounds of the formula I for controlling phytopathogenic bacteria.

The following Examples will serve to illustrate the invention in more detail, but imply no limitation to what is described therein. Parts and percentages are by weight.

PREPARATORY EXAMPLES

EXAMPLE 1

Manufacture of 3-(N-1,3,4-thiadiazolyl-2)-amino-2-methyl-methyl acrylate of the formula

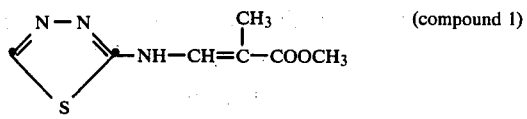
(compound 1)

303 g (3.0 moles) of 2-amino-1,3,4-thiadiazole in 2 liters of methyl cellosolve together with 352.8 g (3.18 moles) of methyl α-formyl-propionate are kept for 16 hours at 120° C. The reaction mixture is cooled and the precipitated crystals are filtered with suction and recrystallised from ethanol. The resultant white crystals melt at 176°–179° C. Concentration of the mother liquor and recrystallisation yield a further amount of the compound No. 1.

EXAMPLE 2

Manufacture of 3-(N-1,3,4-thiadiazolyl-2-N-cyclopropylcarbonyl)-amino-2-methyl-methyl acrylate of the formula

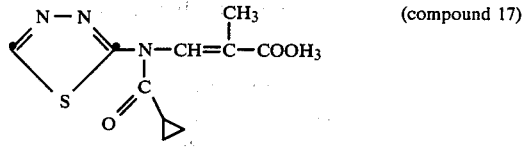
(compound 17)

16.6 g (0.83 mole) of 3-(N-1,3,4-thiadiazolyl-2)-amino-2-methyl-methyl acrylate (compound 1) are added to 200 ml of toluene and then 10.35 g (0.1 mole) of cyclopropanecarboxylic acid chloride are added. The mixture is heated for 18 hours under reflux and, after addition of a small amount of activated carbon, filtered hot. A crude product crystallises out after addition of petroleum ether and is recrystallised from ethanol. Melting point: 116°–118° C.

The following compounds can be prepared by procedures analogous to those described in Examples 1 and 2:

TABLE 1

(I)

| Compound | $R_1$ | $R_2$ | $R_3$ | Physical constant (°C.) |
|---|---|---|---|---|
| 1 | $CH_3$ | $CH_3$ | H | m.p. 176–179° |
| 2 | $C_2H_5$ | $CH_3$ | H | m.p. 186–188° |
| 3 | $n\text{-}C_3H_7$ | $CH_3$ | H | m.p. 131–134° |
| 4 | $n\text{-}C_4H_9$ | $CH_3$ | H | m.p. 143–145° |
| 5 | H | $CH_3$ | H | |
| 6 | $CH_3$ | $C_2H_5$ | H | m.p. 176–179° |
| 7 | $CH_3$ | $n\text{-}C_3H_7$ | H | m.p. 157–160° |
| 8 | $CH_3$ | $n\text{-}C_4H_9$ | H | m.p. 132–133° |
| 9 | $C_2H_5$ | $C_2H_5$ | H | m.p. 162–170° |
| 10 | $CH_3$ | $t\text{-}C_4H_9$ | H | |
| 11 | $i\text{-}C_3H_7$ | $CH_3$ | H | m.p. 138–142° |
| 12 | $n\text{-}C_3H_7$ | $C_2H_5$ | H | m.p. 145–147° |
| 13 | $CH_3$ | $CH_3$ | CO—(2-furyl) | m.p. 118–120° |
| 14 | $CH_3$ | $n\text{-}C_3H_7$ | CO—$CH_2$—Cl | |
| 15 | $CH_3$ | $CH_3$ | CO—$CH_2OCH_3$ | m.p. 119–121° |
| 16 | $CH_3$ | $CH_3$ | CO—$CH_3$ | m.p. 153–157° |
| 17 | $CH_3$ | $CH_3$ | CO—cyclopropyl | m.p. 116–118° |
| 18 | $C_2H_5$ | $CH_3$ | CO—cyclopropyl | |
| 19 | $CH_3$ | $CH_3$ | CO—$C_6H_4$(4-$CH_3$) | m.p. 128–132° |
| 20 | $CH_3$ | $CH_3$ | CO—$C_6H_3(Cl_2 2,4)$ | m.p. 105–109° |
| 21 | $CH_3$ | $CH_3$ | CO—$CH_2Cl$ | m.p. 170–175° |
| 22 | $CH_3$ | $i\text{-}C_3H_7$ | CO—(2-thienyl) | |
| 23 | $CH_3$ | $CH_3$ | CO—CH=$CH_2$ | |
| 24 | $n\text{-}C_3H_7$ | $CH_3$ | CO—$C_6H_3$(3-$NO_2$)(4-Cl) | |
| 25 | $CH_3$ | $CH_3$ | CO—CCl=$CCl_2$ | |
| 26 | $CH_3$ | $CH_3$ | CO—$CH_2CH_3$ | |
| 37 | $CH_3$ | $CH_3$ | CO—cyclohexyl | |
| 28 | $CH_3$ | $CH_3$ | CO—(2,6-dichloropyridyl) | m.p. 140–146° |
| 29 | $CH_3$ | $CH_3$ | CO—$C_6H_4$(3-Cl) | m.p. 124–130° |

Formulation Examples

EXAMPLE 3

Dusts:

The following substances are used to formulate (a) 5%, (b) a 2% and (c) an 80% dust:

(a)
 5 parts of active ingredient
 95 parts of talcum;

(b)

2 parts of active ingredient
1 part of highly dispersed silicic acid
97 parts of talc;

(c)
80 parts of active ingredient
17 parts of talcum
3 parts of highly dispersed silica.

The active ingredients are mixed with the carriers and ground and in this form can be processed to dusts for application.

EXAMPLE 4

Granulate:

The following substances are used to formulate a 5% granulate:
5 parts of actibe ingredient
0.25 part of epoxidised vegetable oil
0.25 part of cetyl polyglycol ether
3.25 parts of polyethylene glycol
91 parts of kaolin (particle size 0.3–0.8 mm).

The active ingredient is mixed with epoxidised vegetable oil and the mixture is dissolved in 6 parts of acetone. Then polyethylene glycol and cetyl polyglycol ether are added. The resultant solution is sprayed on kaolin and the acetone is evaporated in vacuo.

EXAMPLE 5

Wettable powders:

The following constituents are used to formulate (a) a 70%, (b) a 40%, (c) and (d) a 25% and (e) a 10% wettable powder:

(a)
70 parts of active ingredient
5 parts of sodium dibutylnaphthylsulfonate
3 parts of naphthalenesulfonic acid/phenolsulfonic acid/formaldehyde condensate (3:2:1)
10 parts of kaolin
12 parts of Champagne chalk (b)
40 parts of active ingredient
5 parts of sodium ligninsulfonate
1 part of sodium dibutylnaphthalenesulfonic acid
54 parts of silicic acid (c)
25 parts of active ingredient
4.5 parts of calcium ligninsulfate
1.9 parts of Champagne chalk/hydroxyethyl cellulose mixture (1:1)
1.5 parts of sodium dibutylnaphthalenesulfonate
19.5 parts of silicic acid
19.5 parts of Champagne chalk
28.1 parts of kaolin (d)
25 parts of active ingredient
2.5 parts of isooctylphenoxy polyethylene ethanol
1.7 parts of a Champagne chalk/hydroxyethyl cellulose mixture (1:1)
8.3 parts of sodium aluminium silicate
16.5 parts of kieselguhr
46 parts of kaolin (e)
10 parts of active ingredient
3 parts of a mixture of the sodium salts of saturated fatty alcohol sulfates
5 parts of naphthalenesulfonic acid/formaldehyde condensate
82 parts of kaolin.

The active ingredients are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for leaf application.

EXAMPLE 6

Emulsifiable concentrate:

The following substances are used to formulate a 25% emulsifiable concentrate:
25 parts of active ingredient
2.5 parts of epoxidised vegetable oil
10 parts of an alkylarylsulfonate/fatty alcohol polyglycol ether mixture
5 parts of dimethyl formamide
57.5 parts of xylene.

By diluting such a concentrate with water it is possible to prepare emulsions of the desired concentration which are especially suitable for leaf application.

The active ingredients of the formula I can also be applied in the form of such dispersion concentrates with the aid of atomising spray devices.

Biological Examples

EXAMPLE 7

Action against *Xanthomonas oryzae* in rice (a) Residual protective action

Rice plants of the "Caloro" or "S6" variety were reared for 3 weeks in a greenhouse and then sprayed with the test substance in the form of a spray mixture (0.06% of active ingredient). The spray coating was allowed to dry for one day and the treated plants were then put into a climatic chamber at 24° C. and 75–85% relative humidity and infected by severing the tips of the leaves with scissors which had been previously immersed in a suspension of *Xanthomonas oryzae*. After incubation for 10 days in the same room, the cut leaves withered, curled up, and became necrotic. The residual action of the test substance was determined by assessing the extent of these symptoms. The action of compounds 1, 2, 3, 4, 6, 7, 8, 9, 11, 12, 13 and 15 was such that less than 20% of the plants were attacked. Untreated but infected control plants were employed for comparison purposes and exhibited 100% attack.

(b) Systemic action

Rice plants of the "Caloro" or "S6" variety were reared for 3 weeks in a greenhouse and then sprinkled with a suspension of the test substance (0.006% of active ingredient, based on the volume of the soil). Three days after this treatment, the plants were then put into a climatic chamber at 24° C. and 75–85% relative humidity and infected by severing the tips of the leaves with scissors which had been previously immersed in a suspension of *Xanthomonas oryzae*. After incubation for 10 days in the same room, the cut leaves withered, curled up, and became necrotic. The systemic action of the test substance was determined by assessing the extent of these symptoms. In this test, compounds of the formula I, including compounds 1, 2, 3, 4, 6, 7, 8, 9, 11, 12, 13 and 15, reduced attack to less than 20% in comparison to untreated but infected control plants (100% attack).

EXAMPLE 8

Action against *Xanthomonas vesicatoria* in paprika (a) Residual protective action Paprika plants of the "California Wonder" variety were reared for 3 weeks in a greenhouse and then sprayed with the test substance in the form of a spray mixture (0.06% of active ingredient). The spray coating was allowed to dry for one day and the plants were then put into a climatic chamber at 26° C. and 95–100% relative humidity and infected by spraying the undersides of the leaves with a standardised suspension of *Xanthomonas vesicatoria*. After incubation for 6 days in the same room, round, initially wet and later necrotic, specks formed on the leaves. The residual action of the test substance was determined by assessing the size and number of these specks. In this test, compounds of the formula I, including compounds 1, 2, 4, 6, 8, 9, 12, 13 and 15, reduced attack to less than 20% in comparison to untreated but infected control plants (100% attack).

(b) Systemic action

Paprika plants of the "California Wonder" variety were reared for 3 weeks in a greenhouse and then sprayed with the test substance in the form of a spray mixture (0.006% of active ingredient, based on the volume of the soil). Three days after this treatment, the plants were put into a climatic chamber at 26° C. and 95–100% relative humidity and infected by spraying the undersides of the leaves with a standardised suspension of *Xanthomonas vesicatoria*. After incubation for 6 days in the same room, initially wet and later necrotic, specks formed on the leaves. The systemic action of the test substance was determined by assessing the size and number of these specks. In this test, compounds of the formula I, including compounds 1, 2, 4, 7, 9, 11 and 15, reduced attack to less than 20% in comparison to untreated but infected control plants (100% attack).

EXAMPLE 9

Test for possible teratogenic action

Test substances

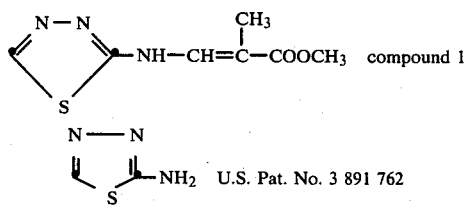

(A) compound 1

(B) U.S. Pat. No. 3 891 762

Pregnant female rats were treated from the 6th to the 15th day of pregnancy either with
- a 0.3% solution of substance A (solution in aqueous sodium carboxymethyl cellulose) in an amount of 1 ml/100 g body weight, or
- a 0.2% solution of substance B (solution in sodium carboxymethyl cellulose/physiological sodium chloride solution) in an amount of 0.5 ml/100 g body weight, or only
- the carrier solution (control).

The animals were sacrificed on the 21st day of gestation and then a count of malformed living foetuses was made.

| Results<br>Total dosage | A<br>30 mg/kg | Control<br>— | B<br>10 mg/kg | Control<br>— |
|---|---|---|---|---|
| embryonal + foetal death in % of the implants | 10.3 | 7.6 | 71.1 | 12.8 |
| number of malformed living foetuses/total number | 0/113 | 0/121 | 26/27 | 0/109 |

What is claimed is:

1. A compound of the formula

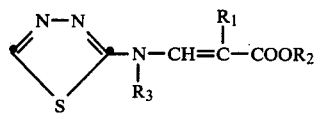

(I)

wherein $R_1$ is hydrogen or $C_1$–$C_4$ alkyl; $R_2$ is $C_1$–$C_4$ alkyl; and $R_3$ is hydrogen or the group —CO—$R_4$ in which $R_4$ is methoxymethyl, $C_3$–$C_6$ cycloalkyl, $C_1$–$C_4$ alkyl optionally mono- or poly-substituted by chlorine, $C_2$–$C_4$ alkenyl optionally mono- or poly-substituted by chlorine, furyl, thienyl, pyridyl or phenyl, the pyridyl or phenyl groups each being optionally mono- to tetrasubstituted by one or more members selected from the group consisting of $C_1$–$C_4$ alkyl, chlorine, cyano and nitro.

2. A compound according to claim 1, wherein $R_3$ is hydrogen.

3. A compound selected from the group consisting of
   3-(N-1,3,4-thiadiazolyl-2)-amino-2-methyl-methyl acrylate,
   3-(N-1,3,4-thiadiazolyl-2)-amino-2-methyl-ethyl acrylate,
   3-(N-1,3,4-thiadiazolyl-2)-amino-2-methyl-n-propyl acrylate,
   3-(N-1,3,4-thiadiazolyl-2)-amino-2-ethyl-ethyl acrylate and
   3-(N-1,3,4-thiadiazolyl-2)-amino-2-isopropyl-methyl acrylate.

4. The compound according to claim 1 which is

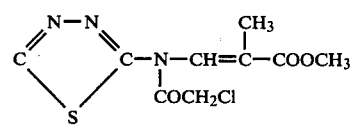

5. The compound according to claim 1 which is

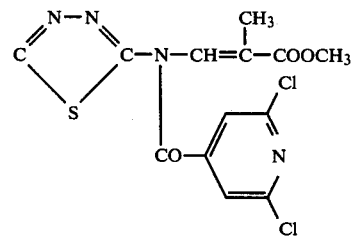

6. A composition for controlling and/or preventing attack by phytopathogenic bacteria, said composition containing, as active component, a bactericidally effective amount of a compound according to claim 1 together with one or more inert carriers or diluents.

7. A composition according to claim 6 which contains, as active component, a compound in which $R_3$ is hydrogen.

8. A composition according to claim 6 which contains, as active component, a compound selected from the group consisting of
- 3-(N-1,3,4-thiadiazolyl-2)-amino-2-methyl-methyl acrylate,
- 3-(N-1,3,4-thiadiazolyl-2)-amino-2-methyl-ethyl acrylate,
- 3-(N-1,3,4-thiadiazolyl-2)-amino-2-methyl-n-propyl acrylate,
- 3-(N-1,3,4-thiadiazolyl-2)-amino-2-ethyl-ethyl acrylate and
- 3-(N-1,3,4-thiadiazolyl-2)-amino-2-isopropyl-methyl acrylate.

9. A method of controlling phytopathogenic bacteria at a locus, which comprises applying to said locus a bacterially effective amount of a compound according to claim 1.

10. A method according to claim 9 in which, in the compound, $R_3$ is hydrogen.

11. A method according to claim 9 in which the compound is selected from the group consisting of
- 3-(N-1,3,4-thiadiazolyl-2-amino-2-methyl-methyl acrylate,
- 3-(N-1,3,4-thiadiazolyl-2)-amino-2-methyl-ethyl acrylate,
- 3-(N-1,3,4-thiadiazolyl-2)-amino-2-methyl-n-propyl acrylate,
- 3-(N-1,3,4-thiadiazolyl-2)-amino-2-ethyl-ethyl acrylate and
- 3-(N-1,3,4-thiadiazolyl-2)-amino-2-amino-2-isopropyl-methyl acrylate.

12. A method according to claim 9, wherein the bacteria controlled are Xanthomonas species.

* * * * *